United States Patent
Weiss

(10) Patent No.: US 9,780,622 B2
(45) Date of Patent: Oct. 3, 2017

(54) LOW FREQUENCY MICRO OSCILLATOR

(71) Applicant: Menachem P. Weiss, Haifa (IL)

(72) Inventor: Menachem P. Weiss, Haifa (IL)

( * ) Notice: Subject to any disclaimer, the term of this patent is extended or adjusted under 35 U.S.C. 154(b) by 0 days.

(21) Appl. No.: 15/114,485

(22) PCT Filed: Feb. 19, 2015

(86) PCT No.: PCT/IL2015/050192
§ 371 (c)(1),
(2) Date: Jul. 27, 2016

(87) PCT Pub. No.: WO2015/125145
PCT Pub. Date: Aug. 27, 2015

(65) Prior Publication Data
US 2016/0352185 A1    Dec. 1, 2016

Related U.S. Application Data

(60) Provisional application No. 61/942,160, filed on Feb. 20, 2014.

(51) Int. Cl.
*H02K 7/075* (2006.01)
*H04M 19/04* (2006.01)
(Continued)

(52) U.S. Cl.
CPC ......... *H02K 7/075* (2013.01); *A61M 25/0043* (2013.01); *H04M 19/047* (2013.01);
(Continued)

(58) Field of Classification Search
CPC ................ H02K 7/075; H04M 19/047; A61M 2202/0007; A61M 2205/00;
(Continued)

(56) References Cited

U.S. PATENT DOCUMENTS

| 6,092,422 A | 7/2000 | Binnig et al. |
| 8,084,898 B2 * | 12/2011 | Kawano ................ H02K 49/10 310/12.14 |
| 2001/0051766 A1 * | 12/2001 | Gazdzinski ........ A61B 1/00016 600/309 |

FOREIGN PATENT DOCUMENTS

| DE | 102011089010 A1 | 6/2013 |
| WO | 2013/121759 A1 | 8/2013 |
| WO | 2015/125145 A1 | 8/2015 |

OTHER PUBLICATIONS

U.S. Appl. No. 61/942,160, filed Feb. 20, 2014.
(Continued)

*Primary Examiner* — Dang Le
(74) *Attorney, Agent, or Firm* — Sughrue Mion, PLLC

(57) ABSTRACT

A low frequency micro oscillator-driven oscillating system including at least one electric oscillation generator operative to produce oscillations at a first frequency, at least one oscillated article, at least one intermediate element, having at least one resonant frequency lower than the first frequency, the at least one intermediate element being oscillated by the at least one electric oscillation generator and being operative to cause the at least one oscillated article to oscillate and a power supply circuit, supplying electrical power intermittently in a periodic manner to the at least one electric oscillation generator, thereby causing the at least one oscillated article to oscillate at at least one second frequency, lower than the first frequency.

20 Claims, 8 Drawing Sheets

(51) Int. Cl.
*A61M 25/00* (2006.01)
*A61B 1/00* (2006.01)
*A61B 1/04* (2006.01)
*A61M 25/01* (2006.01)

(52) U.S. Cl.
CPC ........... *A61B 1/00133* (2013.01); *A61B 1/041* (2013.01); *A61M 25/0111* (2013.01)

(58) Field of Classification Search
CPC ........ A61M 2205/10; A61M 2205/103; A61M 2205/106
See application file for complete search history.

(56) References Cited

OTHER PUBLICATIONS

An International Preliminary Report on Patentability dated Aug. 23, 2016, which issued during the prosecution of Applicant's PCT/IL2015/050192.
An International Search Report dated Jul. 2, 2015, which issued during the prosecution of Applicant's PCT/IL2015/050192.
Written Opinion dated Jul. 2, 2015, which issued during the prosecution of Applicant's PCT/IL2015/050192.

\* cited by examiner

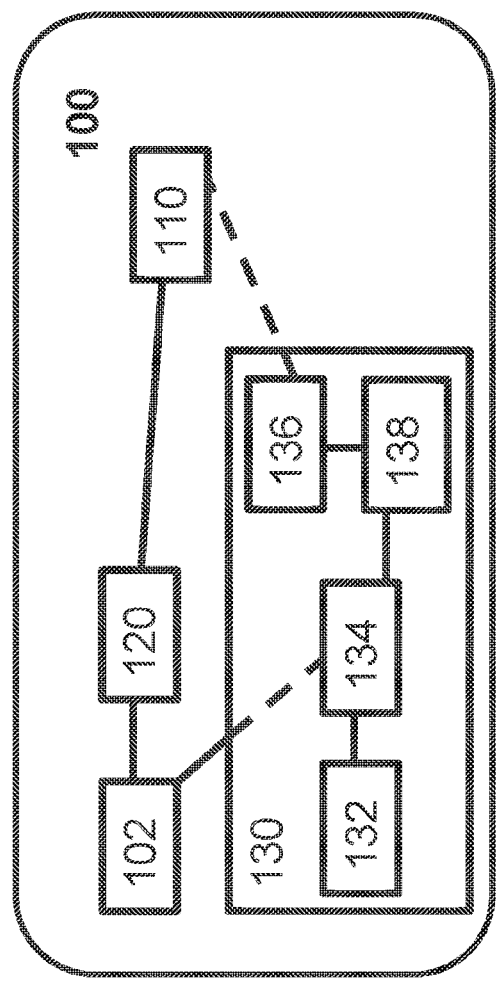

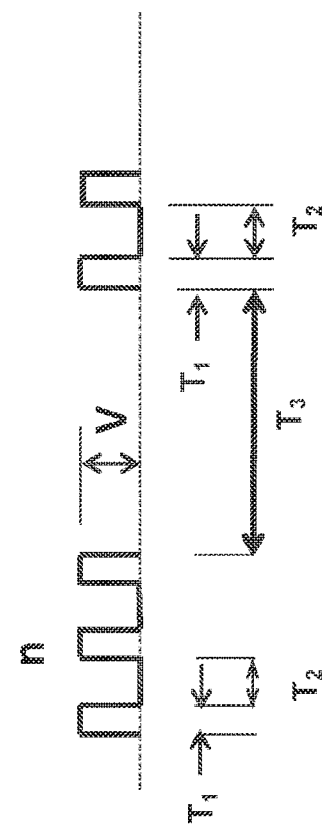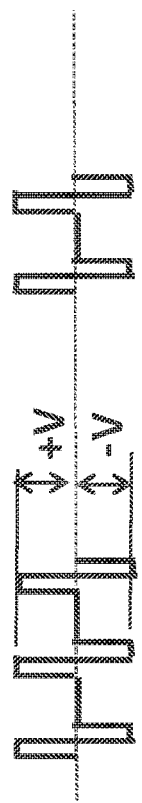

LOW FREQUENCY MICRO OSCILLATOR

REFERENCE TO RELATED APPLICATIONS

Reference is hereby made to U.S. Provisional Patent Application Ser. No. 61/942,160, filed Feb. 20, 2014 and entitled LOWER FREQUENCY VIBRATION GENERATOR, the disclosure of which is hereby incorporated by reference and priority of which is hereby claimed pursuant to 37 CFR 1.78(a) (4) and (5)(i).

FIELD OF THE INVENTION

The present invention relates to oscillators generally and more particularly to micro-oscillators and to systems driven thereby.

BACKGROUND OF THE INVENTION

Various types of micro-oscillators are known.

SUMMARY OF THE INVENTION

The present invention seeks to provide a low frequency micro-oscillator.

There is thus provided in accordance with a preferred embodiment of the present invention a low frequency micro oscillator-driven oscillating system including at least one electric oscillation generator operative to produce oscillations at a first frequency, at least one oscillated article, at least one intermediate element, having at least one resonant frequency lower than the first frequency, the at least one intermediate element being oscillated by the at least one electric oscillation generator and being operative to cause the at least one oscillated article to oscillate and a power supply circuit, supplying electrical power intermittently in a periodic manner to the at least one electric oscillation generator, thereby causing the at least one oscillated article to oscillate at at least one second frequency, lower than the first frequency.

Preferably, at least part of the at least one oscillated article has at least one resonant frequency and at least one of the at least one second frequency is approximately equal to the at least one resonant frequency of the at least part of the at least one oscillated article. Additionally or alternatively, at least one of the at least one second frequency is approximately equal to at least one of the at least one resonant frequency of the at least one intermediate element.

In accordance with a preferred embodiment of the present invention the at least one intermediate element forms part of the at least one oscillated article.

Preferably, the at least one oscillated article oscillates with an amplitude of oscillation which is greater than an amplitude of oscillation of the at least one intermediate element.

In accordance with a preferred embodiment of the present invention the oscillation of the intermediate element is at a frequency close to at least one resonance frequency of at least one of the intermediate element, the at least one oscillated article, a part of the intermediate element and a part of the at least one oscillated article. Alternatively, the at least one second frequency includes a plurality of frequencies in a narrow band frequency range, the narrow band frequency range being selected to include at least one resonance frequency of at least one of the intermediate element, the at least one oscillated article, a part of the intermediate element and a part of the at least one oscillated article.

Preferably, the power supply circuit receives at least one feedback signal from at least one sensor located at at least one of the at least one oscillated article, at least a part of the at least one oscillated article and the intermediate element, and adjusts the oscillation to be at a frequency close to a resonant frequency of at least one of the intermediate element, the at least one oscillated article, a part of the intermediate element and a part of the at least one oscillated article, thereby to control parameters of oscillations of the at least one oscillated article.

In accordance with a preferred embodiment of the present invention the at least one oscillated article is selected from a group consisting of a swallowable capsule that is retained in the stomach, a catheter and an in-vivo implant. Additionally, the low frequency micro oscillator-driven oscillating system also includes a remote control subsystem which enables wireless remote control of the power supply circuit.

In accordance with a preferred embodiment of the present invention the at least one oscillated article is selected from a group consisting of a cellphone, a communication device, a wireless telephone phone, a wired telephone, a computer and a tablet.

Preferably, the power supply circuit supplies electrical power to the at least one electric oscillation generator for a time interval $T_1$ less than 100 milliseconds and thereafter does not supply electrical power to the at least one electric oscillation generator for a time interval $T_2$ less than 100 milliseconds. Additionally, in the time interval $T_2$ electric leads of the electrical oscillation generator are either disconnected from each other or connected to each other.

In accordance with a preferred embodiment of the present invention the at least one electric oscillation generator is selected from a group consisting of: a DC electric motor having an eccentric rotating mass, an electro-magnetic actuator, an electro-static actuator and a linear resonant actuator. Alternatively, the at least on electrical oscillation generator is selected from a group consisting of: a piezo-electric actuator and an AC electric motor having an eccentric rotating mass.

In accordance with a preferred embodiment of the present invention the low frequency micro oscillator-driven oscillating system also includes a remote control subsystem which enables wireless remote control of the power supply circuit.

Preferably, the power supply circuit is directly mechanically and electrically connected to the at least one oscillated article.

In accordance with a preferred embodiment of the present invention the intermediate element is one of the group consisting of a beam, a spring, a membrane, a rigid part and a printed circuit board element.

There is also provided in accordance with another preferred embodiment of the present invention an oscillating mechanism for use with an article sought to be oscillated, the oscillating mechanism including at least one electric oscillation generator operative to produce oscillations at a first frequency, at least one intermediate element, having at least one resonant frequency lower than the first frequency, the at least one intermediate element being oscillated by the at least one electric oscillation generator and being operative to cause the article to oscillate and a power supply circuit, supplying electrical power intermittently in a periodic manner to the at least one electric oscillation generator, thereby causing the article to oscillate at at least one second frequency, lower than the first frequency.

BRIEF DESCRIPTION OF THE DRAWINGS

The present invention will be understood and appreciated more fully from the description which follows with reference to the drawings in which:

FIG. 1 is a simplified illustration of one embodiment of a micro oscillator-driven oscillating system constructed and operative in accordance with a preferred embodiment of the present invention;

FIG. 2A is a simplified voltage versus time diagram of preferred input voltage timing employed in the micro oscillator-driven oscillating system of FIG. 1;

FIG. 2B is a simplified voltage versus time diagram of an alternative input voltage employed in the micro oscillator-driven oscillating system of FIG. 1;

DETAILED DESCRIPTION OF PREFERRED EMBODIMENTS

Figure 3:
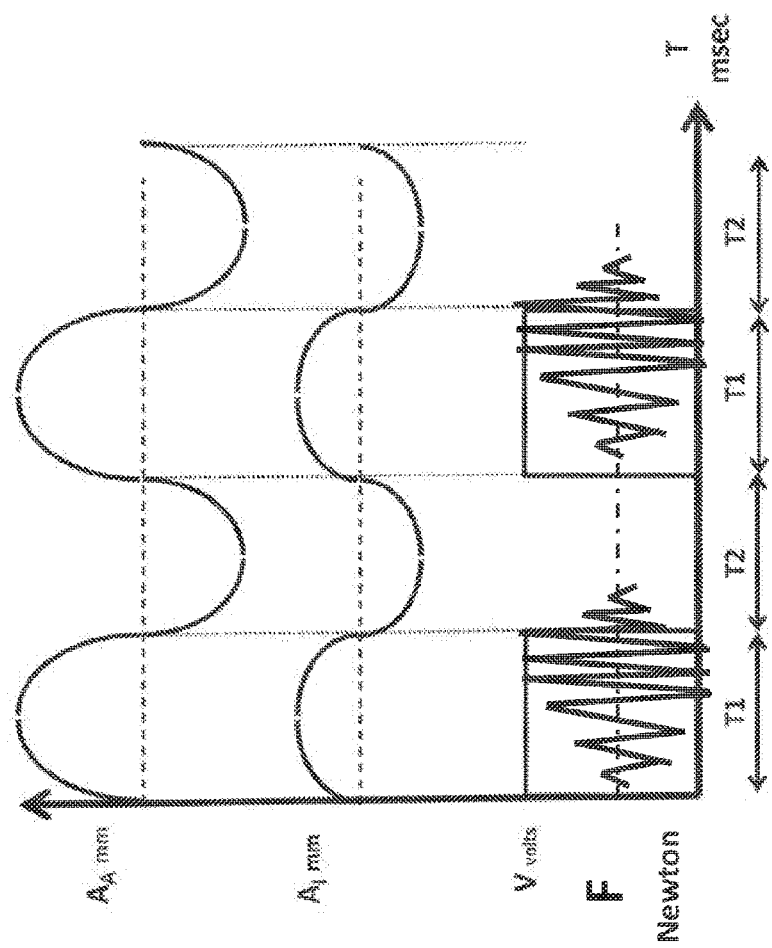
FIG. 3 is a simplified timing and amplitude diagram showing an electrical input to a micro oscillator and corresponding oscillations of an intermediate element and an oscillated article in the embodiment of FIG. 1.

Reference is now made to FIG. 1, which is a simplified illustration of one embodiment of a micro oscillator-driven oscillating system constructed and operative in accordance with a preferred embodiment of the present invention; to FIG. 2A, which is a simplified voltage versus time diagram of preferred input voltage timing employed in the micro oscillator-driven oscillating system of FIG. 1; to FIG. 2B, which is a simplified voltage versus time diagram of an alternative input voltage employed in the micro oscillator-driven oscillating system of FIG. 1; and to FIG. 3, which is a simplified timing and amplitude diagram showing an electrical input to a micro oscillator and corresponding oscillations of an intermediate element and an oscillated article in the embodiment of FIG. 1.

Referring now to FIG. 1, there is seen a low frequency micro oscillator-driven oscillating system 100 constructed and operative in accordance with an embodiment of the present invention and including at least one electric oscillation generator 102, operative to produce oscillations at a first frequency, that is most often greater than 150 Hz. Oscillation generator 102 preferably comprises a DC motor having a rotor and an eccentric mass connected to the rotor. Operation of the motor produces centrifugal forces which produce vibrations. Alternatively, oscillation generator 102 comprises, for example, a piezoelectric element, a solenoid or an electro-static device. Examples of suitable commercially available oscillation generators 102 include the following: C10-100 Haptic, Linear 310-114 and Cylindrical 304-109 all available from PrecisionMicrodrives.com. Z3OCIT8219651 available from JinLong Machinery (Vibramotor.com), piezoelectric actuators available from Physik Instrumente GmbH (www.pi.ws). Typically, the vibration frequencies of most of the oscillation generators useful in embodiments of the present invention are at least 150 Hz.

System 100 preferably includes at least one oscillated article 110, which is sought to be oscillated at a second frequency, which is substantially less than the first frequency, typically in the range of 5-50 Hz. Examples of oscillated articles 110 may be medical devices, such as catheters, swallowable pills and surgical devices and parts thereof and cellular telephones and pagers and parts thereof. The oscillated article preferably has at least one resonant frequency which is preferably the same as the second frequency.

In accordance with a preferred embodiment of the present invention, there is provided at least one intermediate element 120, having a resonant frequency substantially lower than the first frequency, the intermediate element being oscillated by the electric oscillation generator 102 and being operative to cause the at least one oscillated article 110 to oscillate at a frequency less than the first frequency. The at least one intermediate element 120 may have a resonant frequency which is generally the same as that of the at least one oscillated article 110 or alternatively different than that of the at least one oscillated article 110.

Further in accordance with a preferred embodiment of the present invention, the system includes a power supply circuit 130, supplying electrical power intermittently in a periodic manner to the electric oscillation generator 102, thereby causing the oscillated article 110 to oscillate at the second frequency, which is lower than the first frequency. The power supply circuit 130 preferably comprises a power source 132, such as one or more batteries or an inductive power source, and a computerized controller 134, which governs the timing of the supply of electrical power to the electric oscillation generator 102. The power supply circuit 130 may also comprise one or more vibration sensors 136, which sense the oscillations of the oscillated article 110 and output via a feedback circuit 138 to the controller 134 for maintaining a desired oscillation frequency of the oscillated article 110.

Additionally, controller 134 may also include a remote control subsystem which enables wireless remote control of power supply circuit 130.

It is appreciated that in some embodiments of the present invention the power supply circuit 130 is directly mechanically and electrically connected to the at least one oscillated article 110.

FIG. 2A shows preferred input voltage timing employed in the micro oscillator-driven oscillating system of FIG. 1 in accordance with a preferred embodiment of the present invention. In this embodiment, the electric oscillation generator 102 typically has an oscillation frequency of ~180 Hz and is provided with electrical power at a predetermined number of intervals n, each of a duration T1, such as 50 ms, each separated by an interval T2, such as 60 ms, during which no power is provided to the electric oscillation generator 102. For conservation and recuperation of battery power, from time to time, electrical power supply to the electric oscillation generator 102 may be interrupted for a longer time interval T3. In FIG. 2A, the electric power supply is shown to be unipolar, while in FIG. 2B a dual polar electric power supply is shown, with the same timing as in FIG. 2A.

Reference is now made to FIG. 3, which is a simplified timing and amplitude diagram showing an electrical input to a micro oscillator and corresponding oscillations of an intermediate element and an oscillated article in the embodiment of FIG. 1.

In the illustrated example, T1 and T2 each equal 50 ms and the electric oscillation generator 102 operates at about 180 Hz, thus generating approximately 9 oscillations within each 50 ms period. In this example, the generator 102 is a cylindrical vibration motor. The voltage supplied to the generator is shown as a rectangle T1 ms long and V volts high. During interval T1, the rotation of the vibration motor increases gradually from a non-rotation orientation, until it reaches the rated rotation speed of the motor. At the end of interval T1, the voltage supplied to the vibration motor is stopped and the rotation velocity decreases. The rotation of the vibration motor generates a centripetal force F, in Newtons, as shown within the rectangles in FIG. 3. As seen in FIG. 3, the centripetal force increases gradually during interval T1, but declines rapidly during interval T2, when voltage is not supplied to the vibration motor.

It is appreciated that when the electrical leads of electric oscillation generator 102 are electrically connected to one another during the interval T2, when zero voltage is supplied to the vibration motor, the centripetal force F declines even more rapidly than when the electrical leads are not electrically connected. Electrically connecting the electrical leads thus increases the amplitude of the second frequency oscillations induced into the intermediate element 120.

The resulting frequency of vibration, Fr, of the second frequency oscillations that are induced into the intermediate element 120 by the programmed starting and stopping of the electric oscillation generator 102, is approximately equal to 1/(T1+T2). Thus, the sum of T1 and T2 governs the frequency selected. It is appreciated that T1 and T2 are preferably selected so that Fr will be equal to the resonance frequency of the intermediate element 120. It is further appreciated that while the selection of both T1 and T2 govern the frequency of vibration, the selection of T1 alone influences the amplitude of oscillations that is achieved. Furthermore, the selection of T1 is also limited by the power supply characteristics of power source 132 to avoid overstressing power source 132. The amplitude of oscillations of intermediate element 120 in mm is depicted in FIG. 3 as $A_1$.

It is appreciated that the amplitude of oscillations of intermediate element 120 is a function of the interval between starting to supply power to the vibration motor and the vibration motor reaching the rated rotation speed or a maximum desired speed which may be less than the rated rotation speed. Thus, the longer the interval, the greater the amplitude of oscillations of intermediate element 120 that will be generated.

It is appreciated that in some applications, the interval T1 that is selected, during which power is supplied to electric oscillation generator 102, may be shorter than the interval between starting to supply power to the vibration motor and the vibration motor reaching the rated rotation speed or a maximum desired speed which may be less than the rated rotation speed. In this case, the vibration motor will not reach the rated rotation speed or maximum desired speed and the amplitude of oscillations of intermediate element 120 is a function of interval T1.

It is appreciated that in embodiments such as implanted medical devices, the power source 132 is typically a small battery or batteries, which limit the maximum rotation speed that can be achieved and thereby limit the amplitudes of oscillations that can be achieved. In embodiments, such as a cellphone, power source 132 is typically a larger battery or batteries, which can support a longer interval T1 and therefore can generate, by use of the current invention, a much stronger oscillation, without overstressing or draining the power source 132.

The oscillated article 110 typically has the same frequency of vibration as that of the intermediate element 120, depending, inter alia, on their respective resonant frequencies and damping. The system is of two degrees of freedom and has several possible modes of oscillations. The amplitude of a preferred mode of oscillation of the article in mm is depicted as $A_4$. The inventor has found that by suitably selecting system parameters the amplitude of vibration of the oscillated article 110 is significantly higher than that of intermediate element 120, as is shown in the FIG. 3.

Figure 4:
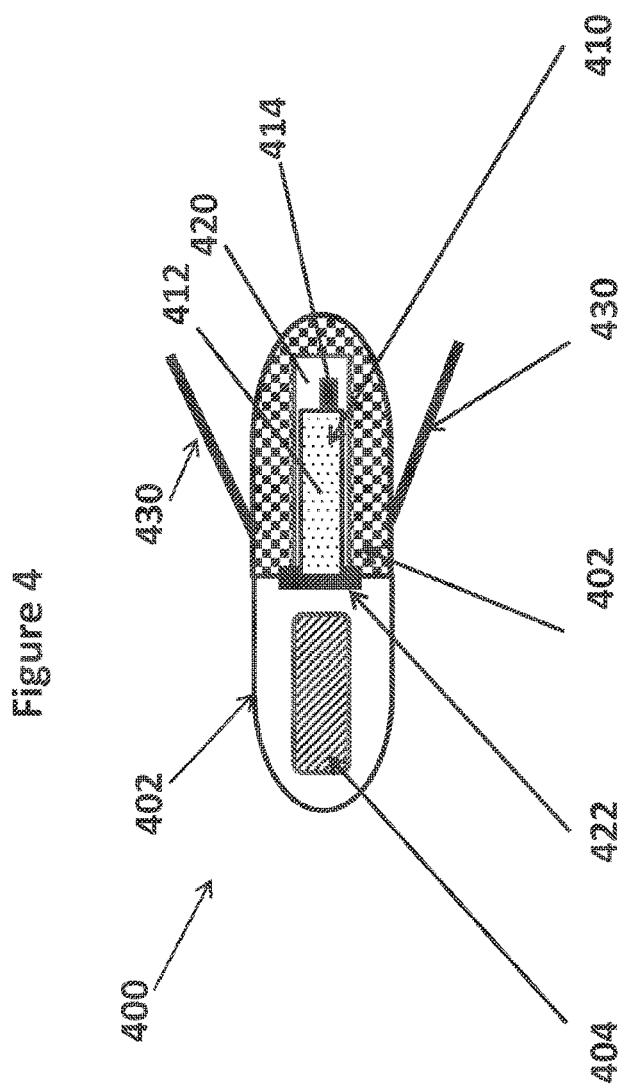
FIG. 4 is a simplified illustration of one embodiment of an arrangement of a micro oscillator, intermediate element and article useful in the embodiment of FIG. 1.

Reference is now made to FIG. 4, which depicts a simplified example of a swallowable pill that generates low frequency vibrations in several appendages thereof. As seen in FIG. 4, a swallowable pill 400 includes a pill housing 402, enclosing a power supply circuit 404, including a power supply and a controller. The controller creates the oscillation parameters and provides the oscillation parameters to an oscillation generator 410, shown in the illustrated embodiment as a motor 412 with an eccentric mass 414 attached. It is appreciated that oscillation generator 410 may be any suitable oscillation generator.

The oscillation generator 410 causes pill housing 402, which serves as the intermediate element, to vibrate. Pill housing 402 is typically a sealed housing that also provides protection to the inner parts of the pill. As seen in FIG. 4, oscillation generator 410 is preferably located in a recess 420 and is connected to pill housing 402 via a connector 422, such as a membrane or a printed circuit board.

Swallowable pill 400 also includes at least one appendage 430, preferably a plurality of appendages 430. Vibration of pill housing 402, which serves as the intermediate element, causes appendages 430, here the articles to be vibrated, to vibrate. In a preferred embodiment of the present invention, appendages 430 are oscillated at a high amplitude at or near the resonant frequency of the appendages.

As described hereinabove with reference to FIG. 1, while the illustrated embodiment of swallowable pill 400 does not show a feedback sensor, swallowable pill 400 may also include a feedback sensor and a feedback circuit connected to the controller.

It is appreciated that while theoretically all of the appendages have the same resonant frequency, in reality, due to manufacturing tolerances, the separate appendages may have somewhat different resonant frequencies. In a first embodiment of swallowable pill 400, all of appendages 430 are constructed to have a resonance frequency close to that of the intermediate element, in this case pill housing 402.

In an alternative embodiment, due to the elongate shape of appendages 430, appendages 430 may be configured to have higher resonance frequencies than pill housing 402. It this alternative embodiment, since appendages 430 are only attached to pill housing 402 at one end thereof, appendages 430 are configured to behave as nearly rigid bodies at the point of attachment to pill housing 402 at the vibration frequency, which is selected to be near the resonant frequency of the pill housing 402, in order to vibrate at a higher amplitude at the end distant from the point of attachment to pill housing 402.

In another alternative embodiment, the connector 422 serves as the intermediate element and the pill housing 402 and appendages 430 together comprise the article to be vibrated.

Figure 5:
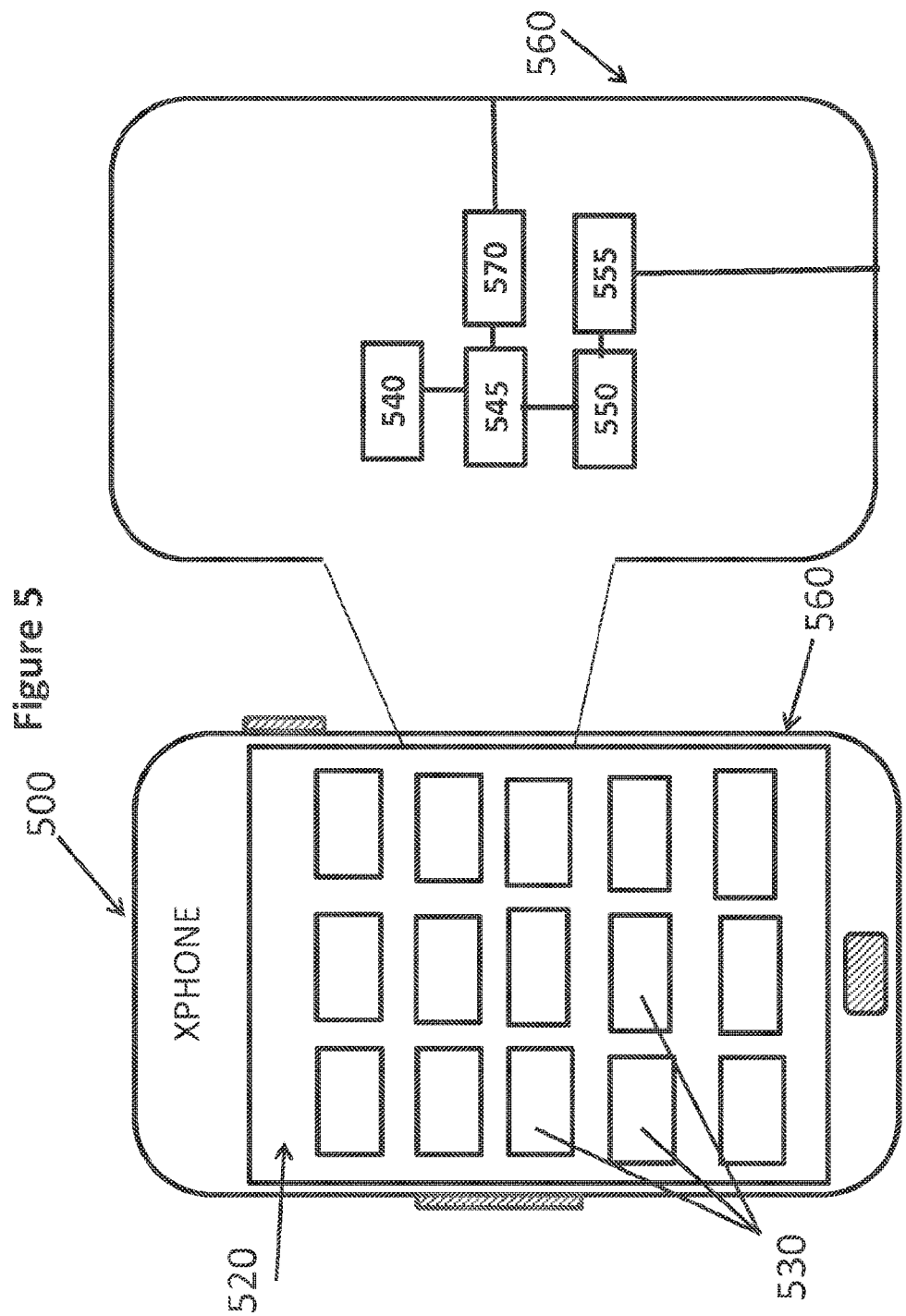
FIG. 5 is a simplified illustration of another embodiment of an arrangement of a micro oscillator, intermediate element and article useful in the embodiment of FIG. 1.

Reference is now made to FIG. 5, which is a simplified illustration of another embodiment of the present invention. As seen in FIG. 5, a cellphone or a tablet 500 typically includes a display 520 and an array of keys 530. Alternatively, the array of keys 530 may be keys that are generated to appear on display 520. The embodiment of FIG. 5 allows different types and strengths of oscillations to be included in cellphone or tablet 500. The oscillation variations allow a user to adjust the oscillation level and mode, for example to better feel the phone vibrating when in a noisy or sporting environment. Additionally, the vibration variations enable different vibrations for different callers, for example, and/or different vibrations signaling different reminders that the user can identify without requiring looking at the display 520.

FIG. 5 also schematically shows some of the internal components of cellphone 500. Cellphone 500 preferably includes a power supply 540, which may be the regular battery of the phone. It is appreciated that the oscillations of the cellphone 500 of the present invention require less power than that used by conventional vibration. Cellphone 500 also includes a controller 545, which forms part of the hardware and software of cellphone 500. Controller 545 controls the electrical generator 550, which oscillates an intermediate element 555, which is a flexible element having a relatively low resonance frequency, an embodiment of which is seen and described hereinbelow with reference to FIG. 6. Intermediate element 555 vibrates main body 560 of cellphone 500, which is the article to be vibrated. Cellphone 500 also includes an oscillation feedback sensor 570 connected to main body 560 of cellphone 500.

Figure 6:
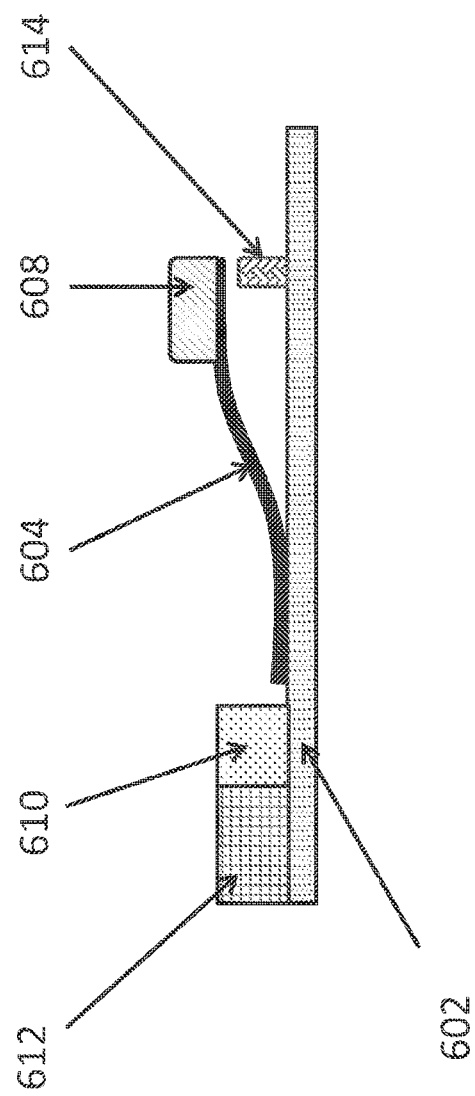
FIG. 6 is a simplified illustration of another embodiment of a micro oscillator-driven oscillating system constructed and operative in accordance with a preferred embodiment of the present invention.

Reference is now made to FIG. 6, which shows an intermediate element useful in embodiments of the present invention, together with some elements of the system of FIG. 1. An article to be vibrated, here designated by reference numeral 602, is connected to an intermediate element 604. An electrical generator 608, preferably in the form of a pancake type vibration motor, is located on the intermediate element 604, a console beam in the illustrated embodiment. Electrical generator 608 may be any other suitable type of generator. Intermediate element 604 may be any suitable type of element, preferably an element that is relatively flexible with at least one low resonance frequency. A controller 610 and a power supply 612 are preferably located on article to be vibrated 602.

As seen in FIG. 6, an additional flexible element 614, preferably a rubber flexible element with damping capability, is located on article to be vibrated 602, preferably in proximity to intermediate element 604 at an end thereof opposite the end where intermediate element 604 is connected to article to be vibrated 602. It is appreciated that intermediate element 604 may be vibrated at multiple vibration frequencies by varying the timing of the power on/off cycles of generator 608. It is a particular feature of the embodiment of FIG. 6 that additional flexible element 614 is located and configured such that additional flexible element 614 operates as a damper on the vibration of intermediate element 604 and thereby generates additional vibration modes.

Figure 7:
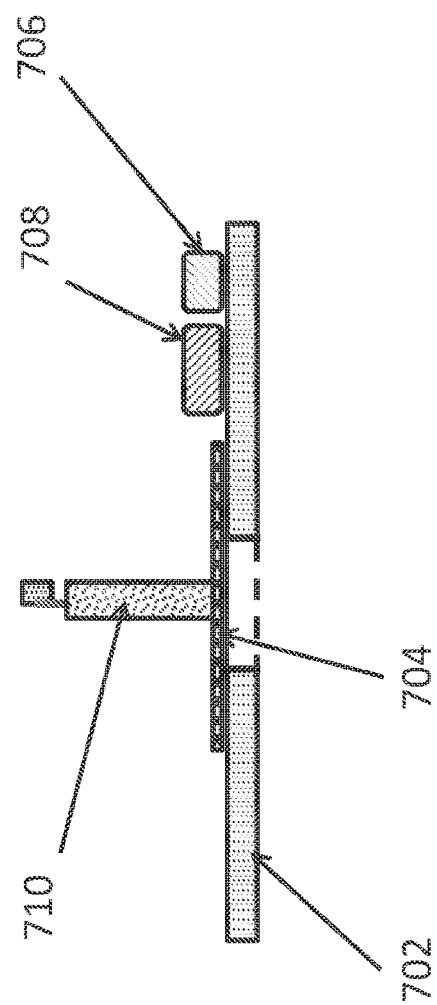
FIG. 7 is a simplified illustration of yet another embodiment of a micro oscillator-driven oscillating system constructed and operative in accordance with a preferred embodiment of the present invention.

Reference is now made to FIG. 7, which illustrates an alternative intermediate element useful in embodiments of the present invention, together with some elements of the system of FIG. 1. As seen in FIG. 7 an article to be vibrated 702 is connected to an intermediate element 704. The embodiment of FIG. 7 also includes a power supply 706, a controller 708 and an electrical oscillation generator 710. In the illustrated embodiment, intermediate element 704 is a printed circuit board. The embodiment shown in FIG. 7 is particularly suitable for very small devices that use Micro-electro-mechanical systems (MEMS) or similar elements.

Figure 8:
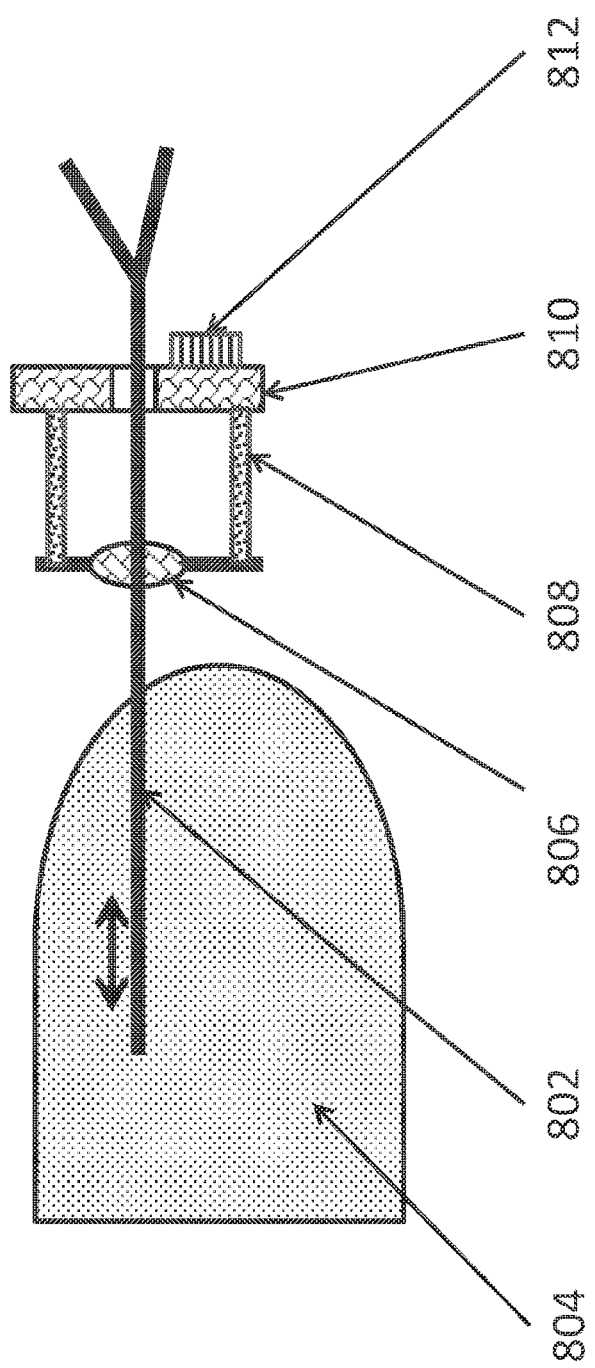
FIG. 8 is a simplified illustration of yet another embodiment of a micro oscillator-driven oscillating system constructed and operative in accordance with a preferred embodiment of the present invention.

Reference is now made to FIG. 8, which illustrates a catheter constructed and operative in accordance with another embodiment of the present invention. It is appreciated that vibration at relatively high amplitudes can protect catheters against bacterial adhesions.

As seen in FIG. 8, a catheter 802 is inserted into a body portion 804 of a patient. An intermediate element 806 is connected to at least one electric oscillation generator 808. Intermediate element 806 is connected to catheter 802, which is the article to be vibrated. In this embodiment, the oscillations are along the length of catheter 802.

A weighted portion 810 preferably serves as a counterweight for vibration transmission to catheter 802, and preferably also includes a power supply circuit 812. Weighted portion 810 also is configured to amplify the oscillation amplitude of intermediate element 806, which in turn amplifies the amplitude of the oscillations of catheter 802.

It will be appreciated by persons skilled in the art that the present invention is not limited by what has been specifically shown and described hereinabove. Rather the scope of the invention includes both combinations and sub-combinations of features described and shown hereinabove as well as modifications thereof which would occur to persons reading the foregoing description and which are not in the prior art.

The invention claimed is:

1. A low frequency micro oscillator-driven oscillating system comprising:
    at least one electric oscillation generator operative to produce oscillations at a first frequency;
    at least one oscillated article;
    at least one intermediate element, having at least one resonant frequency lower than said first frequency, said at least one intermediate element being oscillated by said at least one electric oscillation generator and being operative to cause said at least one oscillated article to oscillate; and
    a power supply circuit, supplying electrical power intermittently in a periodic manner to said at least one electric oscillation generator, thereby causing said at least one oscillated article to oscillate at at least one second frequency, lower than said first frequency.

2. A low frequency micro oscillator-driven oscillating system according to claim 1 and wherein at least part of said at least one oscillated article has at least one resonant frequency and at least one of said at least one second frequency is approximately equal to said at least one resonant frequency of said at least part of said at least one oscillated article.

3. A low frequency micro oscillator according to claim 2 and wherein at least one of said at least one second frequency is approximately equal to at least one of said at least one resonant frequency of said at least one intermediate element.

4. A low frequency micro oscillator according to claim 1 and wherein at least one of said at least one second frequency is approximately equal to at least one of said at least one resonant frequency of said at least one intermediate element.

5. A low frequency micro oscillator-driven oscillating system according to claim 1 and wherein said at least one intermediate element forms part of said at least one oscillated article.

6. A low frequency micro oscillator-driven oscillating system according to claim 1 and wherein said at least one oscillated article oscillates with an amplitude of oscillation which is greater than an amplitude of oscillation of said at least one intermediate element.

7. A low frequency micro oscillator-driven oscillating system according to claim 1 and wherein said oscillation of said intermediate element is at a frequency close to at least one resonance frequency of at least one of said intermediate element, said at least one oscillated article, a part of said intermediate element and a part of said at least one oscillated article.

8. A low frequency micro oscillator according to claim 1, wherein said at least one second frequency comprises a plurality of frequencies in a narrow band frequency range, said narrow band frequency range being selected to include at least one resonance frequency of at least one of said intermediate element, said at least one oscillated article, a part of said intermediate element and a part of said at least one oscillated article.

9. A low frequency micro oscillator-driven oscillating system according to claim 1, wherein said power supply circuit receives at least one feedback signal from at least one sensor located at at least one of said at least one oscillated article, at least a part of said at least one oscillated article and said intermediate element, and adjusts said oscillation to be at a frequency close to a resonant frequency of at least one of said intermediate element, said at least one oscillated article, a part of said intermediate element and a part of said at least one oscillated article, thereby to control parameters of oscillations of said at least one oscillated article.

10. A low frequency micro oscillator-driven oscillating system according to claim 1, wherein said at least one oscillated article is selected from a group consisting of a swallowable capsule that is retained in the stomach, a catheter and an in-vivo implant.

11. A low frequency micro oscillator-driven oscillating system according to claim 10 and also comprising a remote control subsystem which enables wireless remote control of said power supply circuit.

12. A low frequency micro oscillator-driven oscillating system according to claim 1, wherein said at least one oscillated article is selected from a group consisting of a cellphone, a communication device, a wireless telephone phone, a wired telephone, a computer and a tablet.

13. A low frequency micro oscillator-driven oscillating system according to claim 1, wherein said power supply circuit supplies electrical power to said at least one electric oscillation generator for a time interval $T_1$ less than 100 milliseconds and thereafter does not supply electrical power to said at least one electric oscillation generator for a time interval $T_2$ less than 100 milliseconds.

14. A low frequency micro oscillator-driven oscillating system according to claim 13, wherein in said time interval $T_2$ electric leads of said electrical oscillation generator are either disconnected from each other or connected to each other.

15. A low frequency micro oscillator-driven oscillating system according to claim 1, wherein said at least one electric oscillation generator is selected from a group consisting of: a DC electric motor having an eccentric rotating mass, an electro-magnetic actuator, an electro-static actuator and a linear resonant actuator.

16. A low frequency micro oscillator-driven oscillating system according to claim 1, wherein said at least one electrical oscillation generator is selected from a group consisting of: a piezoelectric actuator and an AC electric motor having an eccentric rotating mass.

17. A low frequency micro oscillator-driven oscillating system according to claim 1 and also comprising a remote control subsystem which enables wireless remote control of said power supply circuit.

18. A low frequency micro oscillator-driven oscillating system according to claim 1, wherein said power supply circuit is directly mechanically and electrically connected to the at least one oscillated article.

19. A low frequency micro oscillator-driven oscillating system according to claim 1, wherein said intermediate element is one of the group consisting of a beam, a spring, a membrane, a rigid part and a printed circuit board element.

20. An oscillating mechanism for use with an article sought to be oscillated, said oscillating mechanism comprising:
at least one electric oscillation generator operative to produce oscillations at a first frequency;
at least one intermediate element, having at least one resonant frequency lower than said first frequency, said at least one intermediate element being oscillated by said at least one electric oscillation generator and being operative to cause said article to oscillate; and
a power supply circuit, supplying electrical power intermittently in a periodic manner to said at least one electric oscillation generator, thereby causing said article to oscillate at at least one second frequency, lower than said first frequency.

* * * * *